0
United States Patent
Nishida et al.

(10) Patent No.: US 6,849,112 B2
(45) Date of Patent: Feb. 1, 2005

(54) INORGANIC PARTICLES AS A DENTAL MATERIAL AND A METHOD OF PRODUCING THE SAME

(75) Inventors: Hiroyasu Nishida, Fukuoka-ken (JP); Noboru Senju, Fukuoka-ken (JP); Michio Komatsu, Fukuoka-ken (JP)

(73) Assignee: Catalysts & Chemicals Industries Co., Ltd., Kawasaki (JP)

( * ) Notice: Subject to any disclaimer, the term of this patent is extended or adjusted under 35 U.S.C. 154(b) by 134 days.

(21) Appl. No.: 10/291,550

(22) Filed: Nov. 12, 2002

(65) Prior Publication Data

US 2003/0089276 A1 May 15, 2003

(30) Foreign Application Priority Data

Nov. 13, 2001 (JP) ........................................ 2001-346837

(51) Int. Cl.[7] ................................................. A61K 6/08
(52) U.S. Cl. ........................ 106/35; 106/482; 106/461; 106/483; 106/485; 106/446; 106/431; 423/331; 423/366; 423/327.1
(58) Field of Search .............................. 423/327.1, 331, 423/366; 106/35, 482, 461, 483, 485, 450, 446, 431

(56) References Cited

U.S. PATENT DOCUMENTS 6,042,727 A * 3/2000 Jones et al. ............ 210/500.21

FOREIGN PATENT DOCUMENTS

JP 60-233007 11/1985
JP 7-196428 8/1995

OTHER PUBLICATIONS translation for JP 07–196428.*

* cited by examiner

Primary Examiner—C. Melissa Koslow

(57) ABSTRACT

Amorphous inorganic particles as a dental material includes silica and inorganic oxide(s) other than silica and has high x-ray impermeability. The inorganic particles as a dental material includes silica with the content in the range from 70 to 98 weight % and oxide(s) of one or more elements selected from the group of Zr, Ti, La, Ba, Sr, Hf, Y, Zn, AL, and B, wherein 5 to 70 weight % of the silica is originated from an acidic silicic acid solution and 30 to 95 weight % of the silica is originated from a sol of silica. The inorganic particles as a dental material have an average particle diameter in the range from 1 to 10 μm, specific surface area in the range from 50 to 350 $m^2$/g, pore volume in the range from 0.05 to 0.5 ml/g, amorphous crystallinity as observed by x-ray diffraction, and the refractive index in the range from 1.47 to 1.60.

4 Claims, No Drawings

INORGANIC PARTICLES AS A DENTAL MATERIAL AND A METHOD OF PRODUCING THE SAME

TECHNICAL FIELD

The present invention relates to inorganic particles comprising silica and other inorganic oxides as a dental material and a method of producing the inorganic particles as a dental material.

BACKGROUND TECHNOLOGY

Radiation-impermeable composite materials make it easier to detect marginal deficit or decayed teeth in the tooth tissue adjacent to the hardened composite material when examined with a standard X-ray unit for dental use.

The composite materials for dental use are required to have such characteristics as strength, hardness, and smoothness equivalent to those of a natural tooth, resistance against wearing caused by toothing, compatibility in color tone to natural teeth, appropriate refractive index giving the transparency equivalent to that of natural teeth, and x-ray impermeability which can be differentiated from that of natural teeth. Further it is required that the composite materials can easily be machined.

As the composite material for dental use, for instance, a radiation impermeable composite material for dental use comprising a polymeric resin and non-vitreous micro particles (comprising a homogeneously distributed polycrystalline metal oxide and non-crystalline silicon oxide(s)) is disclosed in Japanese Patent Laid-Open Publication No. SHO 60-233007. In this composite material for dental use, the non-vitreous micro particles contain polycrystalline metal oxides, so that the composite material does not have the transparency equivalent to that of natural teeth. Further when the composite material is heated at a temperature lower than the crystallizing temperature to obtain transparency, strength of the particles becomes insufficient, so that the strength of a tooth repaired with the composite material becomes lower and also the hardness and resistance against wearing caused by toothing sometimes become insufficient.

Japanese Patent Laid-Open Publication No. HEI 7-196428 discloses a non crystalline filler for composite materials for dental use manufactured by aggregating silicon dioxide and other metal oxide(s) and heating the aggregate at a temperature lower than the crystallizing temperature of the metal oxide. This filler (particles) is manufactured by aggregating silicon dioxide and other metal oxide(s), so that the pore volume and strength of the particles can not be controlled, and therefore the transparency can not be improved, or as the adhesiveness thereof to a polymeric resin is not enough, the strength of a tooth repaired with the material becomes lower, and sometimes the hardness and resistance against wearing caused by toothing may be insufficient.

DISCLOSURE OF THE INVENTION

It is an object of the present invention to provide non-crystalline inorganic particles with high x-ray impermeability comprising silica and other inorganic oxide as a dental material, and also to provide a method of manufacturing the inorganic particles as a dental material enabling easy control over a refraction factor, pore volume, and strength of the particles.

The inorganic particles according to the present invention are those comprising 70 to 98 weight % of silica and oxide(s) of one or more elements selected from the group comprising Zr, Ti, La, Ba, Sr, Hf, Y, Zn, Al, and B, and 5–70 weight % of the silica is originated from an acidic silicic acid solution, while 30 to 95 weight % of the silica is originated from a sol of silica.

The inorganic particles as a dental material should preferably have the average particle size in the range from 1 to 10 $\mu$m, the specific surface area in the range from 50 to 350 $m^2/g$, and pore volume in the range from 0.05 to 0.5 ml/g, and the crystallinity observed by x-ray diffraction should preferably be amorphous.

The inorganic particles as a dental material above should preferably have the refractive index in the range from 1.47 to 1.60.

The method of manufacturing the inorganic particles as a dental material with the silica content in the range from 70 to 98 weight % comprises the steps of mixing an acidic silicic acid solution, sol of silica, and a solution of salt(s) of one or more metals selected from the group comprising Zr, Ti, La, Ba, Sr, Hf, Y, Zn, Al, and B, spray-drying the mixture slurry, and heating the dried particles.

In the manufacturing method described above, the mixing step should preferably be performed so that the relation between $SiO_2$ ($S_Z$) in the sol of silica and $SiO_2$ ($S_A$) in the acidic silicic acid solution satisfies the equation of $S_A/(S_A+S_Z)=0.05$ to 0.70.

BEST MODE FOR CARRYING OUT THE INVENTION

Inorganic Particles as a Dental Material

The inorganic particles as a dental material according to the present invention are those comprising silica and other oxide(s), and a content of silica should preferably be in the range from 70 to 98 weight %, and more preferably in the range from 75 to 90 weight %, and the other oxide(s) are those of one or more elements selected from the group comprising Zr, Ti, La, Ba, Sr, Hf, Y, Zn, Al, and B. When the silica contents are less than 70 weight %, crystallization easily occurs, although its possibility varies according to type(s) of oxide(s) other than silica, with the pore volume (porosity) reduced and also adhesiveness to a resin lowered. Also, when crystallization occurs, the, refractive index becomes higher, and when a difference between the refractive index of the inorganic particles and that of a resin becomes larger, the transparency of the dental material is apt to become lower. When the silica contents are over 98 weight %, a quantity of other oxide(s) is too small, and the x-ray impermeability is insufficient.

It is preferable that 5 to 70 weight % of the silica is originated from an acidic silicic acid solution with the remaining portion, namely 30 to 95 weight % of the silica originated from a sol of silica.

When a percentage of the silica originated from an acidic silicic acid solution is less than 5 weight %, such disadvantageous phenomena may occur, for instance, that the silica originated from the silicic acid solution with a low degree of polymerization reacts with the oxide(s) other than silica, which may convert the oxide(s) to particles, and aggregate the particles, and make it impossible to suppress crystallization of the particles. On the other hand, when the percentage of silica originated from the acidic silicic acid solution is over 70 weight %, the pore volume of the obtained inorganic particles becomes smaller, which may in turn lower the adhesiveness to a resin or the refractive index, and when a difference between a refractive index of the inorganic particles and that of a resin becomes larger, the transparency of the dental material is apt to become lower.

In the present invention, an acidic silicic acid solution obtained by dealkylating an alkali metal silicate aqueous solution with an ion-exchange resin or the like or that obtained by hydrolyzing an organic silicate compound with an acid may advantageously be used.

The inorganic particles as a dental material described above contain, in addition to silica, other oxide(s) of one or more elements selected from the group consisting of Zr, Ti, La, Ba, Sr, Hf, Y, Zn, Al, and B. By having the oxide(s) contained, it is possible to obtain the inorganic particles with the x-ray impermeability.

Contents of the oxide(s) other than silica should preferably be in the range from 2 to 30 weight %, and more preferably in the range from 5 to 25 weight %. When the contents of oxide(s) other than silica are less than 2 weight %, the x-ray impermeability is insufficient, and the inorganic particles can not be used as a dental material. When the contents of oxide(s) other than silica are more than 30 weight %, the oxide(s) other than silica will easily be crystallized with the pore volume reduced, and therefore the adhesiveness to a resin becomes lower with the refractive index becoming higher, and when a difference between the refractive index of the inorganic particles and that of a resin becomes larger, the transparency of the obtained mental material is apt to become lower.

The average particle diameter of the inorganic particles as a dental material according to the present invention should preferably be in the range from 1 to 10 $\mu$m, and more preferably in the range from 2 to 8 $\mu$m. When the average particle diameter is less than 1 $\mu$m, strength of the obtained dental material is not sufficient. When the average particle diameter is more than 10 $\mu$m, transparency of the obtained dental material becomes lower, and the unnatural feeling makes people perceive that it is not a natural tooth.

The specific surface area of this inorganic particles should preferably be in the range from 50 to 350 m$^2$/g, and specifically in the range from 100 to 300 m$^2$/g. When the specific surface area is less than 50 m$^2$/g, the inorganic particles have little fine pores, and in that case the adhesiveness to a resin may be insufficient. When the specific surface area is more than 300 m$^2$/g, the diameter of fine pore thereof is too small, and also in that case, the adhesiveness to a resin may be insufficient.

The pore volume of the inorganic particles as a dental material should preferably be in the range from 0.05 to 0.5 ml/g, and more preferably in the range from 0.1 to 0.4 ml/g. When the pore volume is less than 0.05 ml/g, the inorganic particles can not fully absorb the polymeric resin, so that viscosity of a mixture of a resin and the inorganic particles before hardening is low, and sometimes the shape retaining property may be insufficient. On the other hand, when the pore volume is more than 0.5 ml/g, the viscosity of the mixture of a resin and the inorganic particles before hardening is too high, which is apt to lower the shape retaining property and workability.

The inorganic particles according to the present invention should preferably be amorphous when determined by means of the x-ray diffraction. When the inorganic particles are amorphous as determined by the x-ray diffraction, it shows that the oxide(s) other than silica does not crystallize and maintains the state of fine particles, which makes it possible to obtain a dental material having the refractive index in the desired range with excellent transparency.

The inorganic particles as a dental material according to the present invention should preferably have the refractive index in the range from 1.47 to 1.60, and more preferably in the range from 1.48 to 1.55, although the preferable value varies according to a refractive index of a filler resin for dental use which is mixed in the dental material. When the refractive index is less than 1.47 or more than 1.60, the difference between the refractive index of the inorganic particles and that of the filler resin for dental use becomes too large, and in that case the dental material has low transparency, and may give an unnatural feeling making people immediately perceive that the material is different from a natural tooth. The difference between the refractive index of the inorganic particles and that of the filler resin for dental use should preferably be less than 0.03, and more preferably less than 0.01.

Method of Manufacturing Inorganic Particles as a Dental Material

The method of manufacturing the inorganic particles as a dental material according to the present invention comprises the steps of mixing an acidic silicic acid solution, a sol of silica, and a metal salt solution of one or two elements selected from the group comprising Zr, Ti, La, Ba, Sr, Hf, Y, Zn, Al, and B, and heating the dried particles obtained by spray-drying the mixture slurry.

The average particle diameter of silica particles in a sol of silica to be used in the present invention should preferably be in the range from 5 to 50 nm, and more preferably in the range from 5 to 30 nm. When the average particle diameter is less than 5 nm, the mixture slurry containing the sol of silica to be spray-dried may lack the stability, and in that case, the pore volume of the obtained inorganic particles is small, so that the adhesiveness to a resin may become lower and the refractive index becomes higher to degrade the transparency. On the other hand, when the average particle diameter of the silica particles is more than 50 nm, strength of the obtained inorganic particles may be insufficient.

The silica particles may be either non-porous or porous, and the type may be selected according to the necessity. There is not specific restriction over concentration of the sol of silica, and the concentration is ordinary required only to be in the range from 10 to 50 weight % as converted to $SiO_2$.

The acidic silicic acid solution described above may be used in the present invention, and the concentration of acidic silicic acid solution should preferably be in the range from 1 to 10 weight %, and more preferably be in the range from 2 to 5 weight % as converted to $SiO_2$.

Advantageously at first the sol of silica is mixed with the acidic silicic acid solution because of the reasons described above so that the relation between the $SiO_2$ ($S_Z$) originated from the sol of silica and that ($S_A$) satisfies the equation of $S_A/(S_A+S_Z)$=0.05 to 0.70. In other words, blending should be performed so that a content of the silica originated from the acidic silicic acid solution in all silica is in the range from 5 to 70 weight %.

Then an aqueous solution of metal salt of one or more elements selected from the group consisting of Zr, Ti, La, Ba, Sr, Hf, Y, Zn, Al, and B is added as a source of oxides other than silica to this mixture slurry. Such aqueous solution of metal salt as nitrate, chlorate, and sulfate is advantageous, and more specifically such metal salts as zirconium nitrate, ammonium zirconium nitrate, zirconium chloride, zirconium oxychloride, zirconium sulfate, titanium chloride, barium nitrate, aluminum sulfate, zinc chloride, and boric acid may be used.

Concentration of the aqueous solution of metal salt in the mixture slurry with the aqueous solution of metal salt added therein is in the range from 0.5 to 10 weight %, and more specifically in the range from 1 to 8 weight % as converted to oxide. When the concentration is less than 0.5 weight %, a number of particles with the diameter of 1 $\mu$m or less increases with the yield disadvantageously dropped, and on the other hand, when the concentration is 10 weight %, viscosity of the mixture slurry becomes higher with stability of the mixture slurry dropped. Further a number of particles with the particle diameter of 10 $\mu$m or more increases, and when these particles are removed, also the yield drops, and when the slurry is used as it is, transparency of the obtained dental material disadvantageously drops.

Then this mixture slurry is spray-dried. There is no specific restriction over the spray-drying method, but the method making it possible to obtain completely spherical particles with desired size is preferable, and various types of spray-driers based on, for instance, the disk rotation system, and nozzle system may be used. The conditions for drying the mixture slurry may be selected according to such parameters as composition, and stability thereof.

Finally the particles obtained by spray-drying are heated. Although the heating temperature varies according to such factors as types and contents of oxide components other than silica, and a percentage of silica originated from silicic acid solution, it should preferably be in the range from 200 to 1000° C., and more preferably in the range from 500 to 850° C. When the heating temperature is less than 200° C., strength of the inorganic particles is insufficient, and also strength of the dental material obtained by blending the mixture slurry in a resin is low, and the wearing resistance is generally poor. When the heating temperature exceeds 850° C., sometimes the oxide other than silica may crystallize, which makes the dental material's transparency lower and also hardness of the particles higher, and as a result polishing the dental material is difficult, and sometimes artificial tooth with transparency and luster may not be obtained.

The inorganic particles as a dental material obtained as described above have the average particle diameter in the range from 1 to 10 μm, the specific surface area in the range from 50 to 350 m²/g, the pore volume in the range from 0.05 to 0.5 ml/g, and is amorphous when measured by means of x-ray diffraction. The refractive index is in the range from 1.47 to 1.60.

Further the inorganic particles as a dental material obtained as described above may be subjected to the surface processing to improve the dispersibility and adhesiveness to a filler resin for dental use prior to its use. Surface of the inorganic particles may be processed, for instance, by contacting a silane coupling agent such as vinyltrimethoxysilane, or γ-methacryloxy alkyltrimethoxysilane to the particles in the gas phase or liquid phase.

As the inorganic particles as a dental material according to the present invention contain a certain volume of silica originated from an acidic silicic acid solution, the oxides other than silica do not crystalline, and therefore when the inorganic particles are blended with a filler resin for dental use or a resin for hard coating for use, the transparency is excellent, and when the mixture is used as a material for dental use, the material has the transparency equivalent to that of a natural tooth and is excellent in adhesiveness to a resin, strength, hardness, and resistance against wearing in toothing.

With the present invention, it is possible to manufacture economically spherical inorganic particles as a dental material with high transparency which are excellent in adhesiveness to a resin, strength, hardness, and resistance against wearing in toothing and can advantageously be used as a dental material with high transparency.

EXAMPLES

Examples of the present invention are described below, but it should be noted that the present invention is not limited to the examples.

Example 1

Preparation of Inorganic Particles (A)

35 grams of NaOH aqueous solution with concentration of 3 weight % was added to 1867 grams of sol of silica with $SiO_2$ concentration of 3 weight % prepared by diluting a sol of silica (manufactured by CCIC: Cataloid S-20L, average particle Diameter: 17 nm, $SiO_2$ concentration: 10 weight %) to adjust pH to 9.6. Further, the sodium silicate aqueous solution (diluted water glass) with $SiO_2$ concentration of 3.0 weight % was dealkylated with a cation exchange resin to prepare 525 grams of acidic silicic acid solution with $SiO_2$ concentration of 3.0 weight %.

The acidic silicic acid solution and the pH-adjusted diluted sol of silica were mixed together and 41 grams of NaOH aqueous solution with concentration of 3 weight % was added to the mixture to prepare a slurry of the mixture of acidic silicic acid solution and the sol of silica with pH adjusted to 9.6.

Then 394 grams of a ziroconium nitrate aqueous solution (manufactured by Newtechs K.K.: Zircosol AC-7, $ZrO_2$: 4 weight %) was added as a component other than silica to the mixture and the mixture was agitated for 15 minutes to prepare a mixture slurry (A).

Then the mixture slurry was spray-dried at the conditions of an inlet port temperature of the heated air of 80° C., output port temperature of 50° C., and the feed rate of 200 g/minute. The obtained powder was dried for 15 hours under 110° C., and was further heated for 3 hours under 650° C. to prepare the inorganic particles of silica-zirconia (A).

Composition, average particle diameter, specific surface area, pore volume, and refractive index of the obtained particles were measured and also the crystallinity was observed by means of x-ray diffraction, and the results are as shown in Table 1. The diffraction index was measured with an Appe refractive index meter manufactured by Atago K.K.

Further a portion of the inorganic particles of silica-zirconia was heated to and maintained under 800° C. for 2 hours and then the crystallinity was measured by means of x-ray diffraction, and the result is shown also in Table 1.

Assessment of the Transparency 65 weight portions of urethane dimethacrylate and 35 weight portions of triethyleneglycol dimethacrylate were mixed together, and then one weight portion of camphor quinone and two weight portions of dimethylamino ethylmethacrylate were dissolved in the mixture to prepare a polymeric monomer. 70 weight portions of silica-zirconia inorganic particles (A) heated to and maintained under 650° C. for 3 hours was added to 30 weight portions of this polymeric monomer to convert the mixture to a paste. The resultant paste was filled in a teflon dye (of a concave type with the diameter of 15 mm and depth of 2 mm) with a light beam irradiated thereto to obtain a round plate.

This plate was placed on a transparency test sheet divided to a white section and a black section so that a half of the plate is positioned on the black section, and the transparency of the plate on the white section and the black section was observed and was assessed according to the following criteria, and the result is as shown in Table 1.

○: A portion of the plate placed on the black section is black without white turbidity nor reflected light, and also a portion of the plate placed on the white section has the high transparency.

Δ: A portion of the plate placed on the black section is a little whitey, while a portion of the plate placed on the white section is a little colored.

×: A portion of the plate placed on the black section is a little whitey with reflected light, while a portion of the plate placed on the white section is light brown.

Example 2

Preparation of Inorganic Particles (B)

12 grams of NaOH aqueous solution with concentration of 3 weight % was added to 1867 grams of diluted sol of silica with $SiO_2$ concentration of 3 weight % prepared by diluting a sol of silica (manufactured by CCIC, Cataloid S-20L, average particle diameter: 17 nm, $SiO_2$: 10 weight %) to adjust pH to 9.6. Further, a sodium silicate aqueous solution with $SiO_2$ concentration of 3.0 weight % was dealkylated with a cation exchange resin to prepare 602 grams of silicic acid solution with $SiO_2$ concentration of 3.0 weight %.

This acidic silicic acid solution and the pH-adjusted sol of silica were mixed together, and 47 grams of NaOH aqueous solution with concentration of 3 weight % was added to the mixture to prepare a mixture slurry of acidic silicic acid solution and sol of silica with pH adjusted to 9.6.

407 grams of a zirconium nitrate aqueous solution (manufactured by Newtechs K.K.: Zircosol AC-7, $ZrO_2$: 4 weight %) was added to the mixture as a component other than silica, and the resultant mixture was agitated for 15 minutes to prepare a mixture slurry (B).

Then the mixture was spray-dried and heated in the same manner as that in Example 1 to prepare inorganic particles of silica-zirconia (B).

Example 3

Preparation of Inorganic Particles (c)

12 grams of NaOH aqueous solution with concentration of 3 weight % was added to 1867 grams of diluted sol of silica with $SiO_2$ concentration of 3 weight % prepared by diluting a sol of silica (manufactured by CCIC, Cataloid S-20L, average particle diameter: 17 nm, $SiO_2$: 10 weight %) to adjust pH to 9.6. Further, a sodium silicate aqueous solution with $SiO_2$ concentration of 3.0 weight % was dealkylated with a cation exchange resin to prepare 3360 grams of silicic acid solution with $SiO_2$ concentration of 3.0 weight %.

This acidic silicic acid solution and the pH-adjusted sol of silica were mixed together, and 261 grams of NaOH aqueous solution with concentration of 3 weight % was added to the mixture to prepare a mixture slurry of acidic silicic acid solution and sol of silica with pH adjusted to 9.6.

407 grams of a zirconium nitrate aqueous solution (manufactured by Newtechs K.K.: Zircosol AC-7, $ZrO_2$: 4 weight %) was added to the mixture as a component other than silica, and the resultant mixture was agitated for 15 minutes to prepare a mixture slurry (C).

Then the mixture was spray-dried and heated in the same manner as that in Example 1 to prepare inorganic particles of silica-zirconia (C).

Example 4

Preparation of Inorganic Particles (D)

12 grams of NaOH aqueous solution with concentration of 3 weight % was added to 1867 grams of diluted sol of silica with $SiO_2$ concentration of 3 weight % prepared by diluting a sol of silica (manufactured by CCIC, Cataloid S-20L, average particle diameter: 17 nm, $SiO_2$: 10 weight %) to adjust pH to 9.6. Further, a sodium silicate aqueous solution with $SiO_2$ concentration of 3.0 weight % was dealkylated with a cation exchange resin to prepare 363 grams of silicic acid solution with $SiO_2$ concentration of 3.0 weight %.

This acidic silicic acid solution and the pH-adjusted sol of silica were mixed together, and 28 grams of NaOH aqueous solution with concentration of 3 weight % was added to the mixture to prepare a mixture slurry of acidic silicic acid solution and sol of silica with pH adjusted to 9.6.

272 grams of a zirconium nitrate aqueous solution (manufactured by Newtechs K.K.: Zircosol AC-7, $ZrO_2$: 4 weight %) was added to the mixture as a component other than silica, and the resultant mixture was agitated for 15 minutes to prepare a mixture slurry (D).

Then the mixture was spray-dried and heated in the same manner as that in Example 1 to prepare inorganic particles of silica-zirconia (D).

Example 5

Preparation of Inorganic Particles (E)

12 grams of NaOH aqueous solution with concentration of 3 weight % was added to 1867 grams of diluted sol of silica with $SiO_2$ concentration of 3.5 weight % prepared by diluting a sol of silica (manufactured by CCIC, Cataloid S-20L, average particle diameter: 17 nm, $SiO_2$: 10 weight %) to adjust pH to 9.6. Further, a sodium silicate aqueous solution with $SiO_2$ concentration of 3.0 weight % was dealkylated with a cation exchange resin to prepare 603 grams of silicic acid solution with $SiO_2$ concentration of 3.0 weight %.

This acidic silicic acid solution and the pH-adjusted sol of silica were mixed together, and 47 grams of NaOH aqueous solution with concentration of 3 weight % was added to the mixture to prepare a mixture slurry of acidic silicic acid solution and sol of silica with pH adjusted to 9.6.

302 grams of a zirconium nitrate aqueous solution (manufactured by Newtechs K.K.: Zircosol AC-7, $ZrO_2$: 4 weight %) was added to the mixture as a component other than silica, and the resultant mixture was agitated for 15 minutes to prepare a mixture slurry (E).

Then the mixture was spray-dried and heated in the same manner as that in Example 1 to prepare inorganic particles of silica-zirconia (E).

Example 6

Preparation of Inorganic Particles (F)

12 grams of NaOH aqueous solution with concentration of 3 weight % was added to 1867 grams of diluted sol of silica with $SiO_2$ concentration of 3.62 weight % prepared by diluting a sol of silica (manufactured by CCIC, Cataloid S-20L, average particle diameter: 17 nm, $SiO_2$: 10 weight %) to adjust pH to 9.6. Further, a sodium silicate aqueous solution with $SiO_2$ concentration of 3.0 weight % was dealkylated with a cation exchange resin to prepare 718 grams of silicic acid solution with $SiO_2$ concentration of 3.0 weight %.

This acidic silicic acid solution and the pH-adjusted sol of silica were mixed together, and 56 grams of NaOH aqueous solution with concentration of 3 weight % was added to the mixture to prepare a mixture slurry of acidic silicic acid solution and sol of silica with pH adjusted to 9.6.

754 grams of a zirconium nitrate aqueous solution (manufactured by Newtechs K.K.: Zircosol AC-7, $ZrO_2$: 4 weight %) was added to the mixture as a component other than silica, and the resultant mixture was agitated for 15 minutes to prepare a mixture slurry (F).

Then the mixture was spray-dried and heated in the same manner as that in Example 1 to prepare inorganic particles of silica-zirconia (F).

Example 7

Preparation of Inorganic Particles (G)

Inorganic particles of silica-titanium (G) were prepared in the same manner as that in Example 1 except the fact that the titanium sulfate aqueous solution (with $Ti(SO_4)_2$ concentration of 12 weight % and with the concentration of 4 weight % as converted to $TiO_2$) was prepared by diluting a titanium sulfate aqueous solution (manufactured by Kanto Kagaku K.K.: with $Ti(SO_4)_2$ concentration of 24 weight % and with the concentration of 8 weight % as converted to $TiO_2$) as a component other than silica.

Comparative Example 1

Preparation of Inorganic Particles (H)

12 grams of NaOH aqueous solution with concentration of 3 weight % was added to 1867 grams of diluted sol of silica with $SiO_2$ concentration of 3.5 weight % prepared by diluting a sol of silica (manufactured by CCIC, Cataloid S-20L, average particle diameter: 17 nm, $SiO_2$: 10 weight %) to adjust pH to 9.6.

307 grams of a zirconium nitrate aqueous solution (manufactured by Newtechs K.K.: Zircosol AC-7, $ZrO_2$: 4 weight %) was added to the mixture as a component other than silica, and the resultant mixture was agitated for 15 minutes to prepare a mixture slurry (H).

Then the mixture was spray-dried and heated in the same manner as that in Example 1 to prepare inorganic particles of silica-zirconia (H).

Comparative Example 2

Preparation of Inorganic Particles (I)

12 grams of NaOH aqueous solution with concentration of 3 weight % was added to 1867 grams of diluted sol of silica with $SiO_2$ concentration of 3.5 weight % prepared by diluting a sol of silica (manufactured by CCIC, Cataloid S-20L, average particle diameter: 17 nm, $SiO_2$: 10 weight %) to adjust pH to 9.6.

545 grams of a zirconium nitrate aqueous solution (manufactured by Newtechs K.K.: Zircosol AC-7, $ZrO_2$: 4 weight %) was added to the mixture as a component other than silica, and the resultant mixture was agitated for 15 minutes to prepare a mixture slurry (I).

Then the mixture was spray-dried and heated in the same manner as that in Example 1 to prepare inorganic particles of silica-zirconia (I).

Comparative Example 3

Preparation of Inorganic Particles (J)

Inorganic particles of silica-titanium (J) were prepared in the same manner as that in Comparative example 1 except the fact that the titanium sulfate aqueous solution (with $Ti(SO_4)_2$ concentration of 12 weight % and with the concentration of 4 weight % as converted to $TiO_2$) was prepared by diluting a titanium sulfate aqueous solution (manufactured by Kanto Kagaku K.K.: with $Ti(SO_4)_2$ concentration of 24 weight % and with the concentration of 8 weight % as converted to $TiO_2$) as a component other than silica.

Comparative Example 4

Preparation of Inorganic Particles (K)

The inorganic particles of silica-zirconia (K) were prepared in the same manner as that in Example 1 except the point that 70 grams of acidic silicic acid solution with $SiO_2$ concentration of 3.0 weight % and 318 grams of the zirconium nitrate aqueous solution were used.

TABLE 1

| | Composition of mixture slurry | | | |
|---|---|---|---|---|
| | silica sol | s.a. sltn | other oxide | | p.diameter |
| | (wt %) | (wt %) | | (wt %) | (µm) |
| Example 1 | 64 | 18 | $ZrO_2$ | 18 | 3.5 |
| Example 2 | 62 | 20 | $ZrO_2$ | 18 | 3.7 |
| Example 3 | 30 | 54 | $ZrO_2$ | 16 | 3.5 |
| Example 4 | 72 | 14 | $ZrO_2$ | 14 | 4.0 |
| Example 5 | 65 | 21 | $ZrO_2$ | 14 | 3.0 |
| Example 6 | 52 | 20 | $ZrO_2$ | 28 | 3.3 |
| Example 7 | 64 | 18 | $TiO_2$ | 18 | 3.5 |
| Com. Ex 1 | 82 | — | $ZrO_2$ | 18 | 3.4 |
| Com. Ex 2 | 72 | — | $ZrO_2$ | 28 | 3.5 |
| Com. Ex 3 | 82 | — | $TiO_2$ | 18 | 3.5 |
| Com. Ex 4 | 79 | 3 | $ZrO_2$ | 18 | 3.5 |

TABLE 1-bis

| | Inorganic particles | | | | | |
|---|---|---|---|---|---|---|
| | s. area | p. vol. | ref index | crystallinity(*1) | | transparency |
| | $(m^2/g)$ | (ml/g) | | 650° C. | 800° C. | |
| Example 1 | 150 | 0.25 | 1.52 | A | A | ○ |
| Example 2 | 173 | 0.19 | 1.52 | A | A | ○ |
| Example 3 | 260 | 0.27 | 1.51 | A | A | ○ |
| Example 4 | 175 | 0.27 | 1.51 | A | A | ○ |
| Example 5 | 167 | 0.15 | 1.51 | A | A | ○ |
| Example 6 | 176 | 0.12 | 1.53 | A | A | ○ |
| Example 7 | 165 | 0.16 | 1.54 | A | A | ○ |
| Com. Ex 1 | 180 | 0.18 | 1.53 | C | C | Δ |
| Com. Ex 2 | 160 | 0.15 | 1.55 | C | C | x |
| Com. Ex 3 | 155 | 0.17 | 1.54 | C | C | Δ |
| Com. Ex 4 | 155 | 0.17 | 1.54 | C | C | Δ |

(*1) A: amorphous C: Crystalline

What is claimed is:

1. Inorganic particles as a dental material comprising silica in a range from 70 to 98 weight % and at least one oxide of at least one element selected from the group consisting of Zr, Ti, La, Ba, Sr, Hf, Y, Zn, AL, and B, wherein 5 to 70 weight % of the silica is originated from an acidic silicic acid solution and 30 to 95 weight % of the silica is originated from a sol of silica, said inorganic particles having an average particle diameter in a range from 1 to 10 µm, specific surface area in a range from 50 to 350 $m^3/g$, pore volume in a range from 0.05 to 0.5 ml/g and amorphous crystallinity as observed by x-ray diffraction.

2. The inorganic particles as a dental material according to claim 1, wherein a refractive index is in a range from 1.47 to 1.60.

3. A method of manufacturing inorganic particles as a dental material with a silica content in a range from 70 to 98 weight % comprising the steps of:

mixing an acidic silicic acid solution, a sol of silica, and an aqueous solution of metal salt of one or more elements selected from the group consisting of Zr, Ti, La, Ba, Sr, Hf, Y, Zn, AL, and B;

spray-drying a mixture slurry; and heating obtained particles.

4. The method of manufacturing inorganic particles as a dental material according to claim 3, wherein the mixing is performed so that a relation between $SiO_2$ ($S_Z$) in the sol of silica and $SiO_2$ ($S_A$) in the acidic silicic acid solution satisfies an equation of $S_A/(S_A+S_Z)=0.05$ to 0.70.

* * * * *